(12) United States Patent
Sogabe et al.

(10) Patent No.: US 11,439,582 B2
(45) Date of Patent: Sep. 13, 2022

(54) LOW-STRINGINESS THICKENER AND COSMETIC MATERIAL ADMIXED WITH SAID THICKENER

(71) Applicant: SHISEIDO COMPANY, LTD., Tokyo (JP)

(72) Inventors: Atsushi Sogabe, Yokohama (JP); Ayano Matsuo, Yokohama (JP); Shin-Ichi Yusa, Himeji (JP)

(73) Assignee: SHISEIDO COMPANY, LTD., Tokyo (JP)

( * ) Notice: Subject to any disclaimer, the term of this patent is extended or adjusted under 35 U.S.C. 154(b) by 0 days.

(21) Appl. No.: 15/784,337

(22) Filed: Oct. 16, 2017

(65) Prior Publication Data
US 2018/0036221 A1 Feb. 8, 2018

Related U.S. Application Data

(62) Division of application No. 15/028,134, filed as application No. PCT/JP2013/077521 on Oct. 9, 2013, now abandoned.

(51) Int. Cl.
| | |
|---|---|
| A61K 8/81 | (2006.01) |
| A61Q 19/00 | (2006.01) |
| C08F 120/06 | (2006.01) |
| C08F 8/44 | (2006.01) |
| C08F 120/58 | (2006.01) |

(52) U.S. Cl.
CPC .......... *A61K 8/8147* (2013.01); *A61K 8/8152* (2013.01); *A61K 8/8158* (2013.01); *A61Q 19/00* (2013.01); *C08F 8/44* (2013.01); *C08F 120/06* (2013.01); *C08F 120/58* (2013.01); *A61K 2800/10* (2013.01); *A61K 2800/48* (2013.01)

(58) Field of Classification Search
CPC ............ A61K 2800/10; A61K 2800/48; A61K 8/8147; A61K 8/8152; A61K 8/8158; A61Q 19/00; C08F 120/06; C08F 120/58; C08F 8/44
See application file for complete search history.

(56) References Cited

U.S. PATENT DOCUMENTS

| | | | |
|---|---|---|---|
| 4,065,422 A | 12/1977 | Lundmark et al. | |
| 5,221,722 A * | 6/1993 | Sehm | A61K 8/8147 523/111 |
| 5,721,275 A | 2/1998 | Bazzano | |
| 6,986,895 B2 | 1/2006 | Suares et al. | |
| 7,449,439 B2 * | 11/2008 | Ito | C11D 3/042 510/191 |
| 2003/0118619 A1* | 6/2003 | Suares | A61K 8/365 424/401 |
| 2005/0196364 A1* | 9/2005 | Josso | A61K 8/8158 424/59 |
| 2013/0157901 A1 | 6/2013 | Ogle et al. | |

FOREIGN PATENT DOCUMENTS

| | | |
|---|---|---|
| JP | H 09-71602 | 3/1997 |
| JP | 2005-274350 | 10/2005 |
| JP | 2008088290 | 4/2008 |
| JP | 2010-270168 | 12/2010 |
| JP | 2011-002418 | 1/2011 |
| JP | 2013-180997 | 9/2013 |
| WO | WO 98/01479 | 1/1998 |

OTHER PUBLICATIONS

Robert Y. Lochhead "Poly(acrylic acid) Thickeners", Polymers in Aqueous Media Advances in Chemistry; American Chemical Society: Washington, DC, 1989. (Year: 1989).*
Sumerlin : Water-Soluble Polymers. 84. Controlled Polymerization in Aqueous Media of Anionic Acrylamido Monomers via RAFT Macromolecules 2001, 34, 6561-6564 (Year: 2001).*
Yusa et al "Synthesis of Thermo-Responsive 4-Arm Star-Shaped Porphyrin-Centered Poly(N,N-diethylacrylamide) via Reversible Addition-Fragmentation Chain Transfer Radical Polymerization", 2009 (Year: 2009).*
Molar mass distribution—Wikipedia; retrieved Dec. 26, 2020 (Year: 2020).*
Introduction to Plastics and Polymers , 2013 (Year: 2013).*
Peter Kay et al "The Intrinsic Viscosity of Poly(acrylic acid) at Different Ionic Strengths : Random Coil and Rigid Rod Behaviour", Die Makromolekulare Chemie 175, 3207-3223 (1974) (Year: 1974).*
Japanese Examination Report dated Jan. 3, 2017, Pat. Appln. No. 102136717, 3 pages—English, 4 pages—Japanese.
Chinese Citation, 1 page—English, 4 pages—Chinese, dated Nov. 8, 2016.
Journal of Polymer Science Part A: Polymer Chemistry, vol. 47, Issue 24, Dec. 15, 2009, pp. 6827-6838, "Synthesis of thermo-responsive 4-arm star-shaped porphyrin-centered poly(N,N-diethylacrylamide) via reversible addition-fragmentation chain transfer radical polymerization"; by Shin-Ichi Yusa; Endo; Ito; published Nov. 5, 2009; Wiley Online Library, Copyright 1999-2016, John Wiley & Sons, Inc.
Macromolecules, 2001, 34(7), pp. 2248-2256, published Feb. 17, 2001, Copyright 2001 American Chemical Society; Water-Soluble Polymers, 81, Direct Synthesis of Hydrophilic Styrenic-Based Homopolymers and Block Copolymers in Aqueous Solution via RAFT, by Mitsukami, Donovan, Lowe, McCormick, Dept. of Polymer Science, University of Southern Mississippi, Hattiesburg, Miss.

(Continued)

*Primary Examiner* — Ling Siu Choi
*Assistant Examiner* — Gennadiy Mesh
(74) *Attorney, Agent, or Firm* — Andrew F. Young; Nolte Lackenbach Siegel (57) ABSTRACT

Aqueous compositions can be thickened without increasing stringiness, by using polymers of polyacrylic acid, poly(2-acryamide-2-methylpropanesulfonate), or salts thereof, having a weight average molecular weights of 500,000 to 8,000,000 as thickeners. The polymers contain no more than 10 mass % of polymers having a molecular weight of 10,000,00 or more, and/or contain no more than 10 mass % of polymers having more than three times the weight average molecular weight. Aqueous solutions of these polymers exhibit a low degree of stringiness, and are particularly useful as thickeners for cosmetics.

8 Claims, 1 Drawing Sheet

(56) References Cited

OTHER PUBLICATIONS

EP 13895394.8, Extended European Search Report dated Jun. 16, 2017, 6 pages—English.
KR 10-2016-7005050, Korean Office Action dated Oct. 22, 2019, 4 pages—English, 5 pages—Korean.

* cited by examiner

LOW-STRINGINESS THICKENER AND COSMETIC MATERIAL ADMIXED WITH SAID THICKENER

CROSS REFERENCE TO PRIORITY CLAIM

This application is a divisional of U.S. Ser. No. 15/028,134 filed Apr. 8, 2016, the entire contents of which are incorporated herein by reference, which in turn claims priority from § 371 national phase of Ser. No. :PCT/JP2013/077521 filed Oct. 9, 2013, the entire contents of which are incorporated herein by reference.

TECHNICAL FIELD

The present invention relates to a less stringiness thickener suitable for cosmetics and a cosmetic admixed with the said thickeners.

BACKGROUND ART

Normally, various kinds of thickeners are blended in cosmetics for the realization of a viscosity suitable for use, the improvement in the feeling in use, and the stabilization of emulsion systems. Many of them are water-soluble polymer compounds and classified, depending upon their origins, into natural polymers (xanthan gum, hyaluronic acid, etc.), semi-synthetic polymers in which functional groups are added to natural polymers by synthesis reactions, and synthetic polymers. Among them, natural polymer compounds have issues such as supply stability and quality stability (lot-dependent viscosity variation, contamination by microorganisms, etc.); thus the demand for synthetic polymer compounds is becoming high in recent years.

These polymer compounds are generally considered to exert a thickening effect by taking in water molecules into the molecules (namely, hydration) and the formation of a three-dimensional network structure. In many cases, the stringiness (i.e., long, thin, sinewy) property appears with an increase in viscosity. The stringiness property can be a cause of sliminess, stickiness, and poor spreadability; therefore, it is a property that we normally want to eliminate from cosmetic raw materials. As described above, the stringiness property becomes pronounced with an increase in viscosity; however, it is also highly dependent on the elasticity of polymer compounds. Thus, the property is considered to be not necessarily separable from the thickening effect exerted by polymer compounds. In particular, there is a report that the degree of the stringiness property felt by the human skin (this is called "stringy feeling" in this application) is not correlated with the viscosity of test materials (PTL 1).

Therefore, various efforts have been made, in the field of cosmetics, to reduce the stringiness property of thickeners. For example, it is reported in the case of natural polymer polysaccharide compounds, such as carrageenan and xanthan gum, that the stringiness property can be reduced, without losing the thickening effect of polymer compounds, by allowing a specific percentage of a specific organic acid to coexist (PTL 2). In the case of hyaluronic acid, which is also a polysaccharide, it is shown that the stringiness property can be reduced, so far as it is a relatively low-molecular hyaluronic acid, by substituting a part of the alcoholic hydroxyl groups with acetyl groups (PTL 3).

However, these methods lack versatility, and it is difficult to say that they are effective methods even for synthetic polymer compounds, which are used frequently in cosmetics. In particular, polyacrylic acid or a salt thereof, or poly(2-acrylamido-2-methylpropanesulfonic acid) (hereinafter abbreviated as PAMPS) or a salt thereof has widely been used as a thickener because of the excellent water-absorbing property/thickening effect. However, the stringiness property is very strong; thus the blending quantity is restricted. Accordingly, a method to reduce the stringiness property of these synthetic polymer compounds has particularly been demanded.

PRIOR ART DOCUMENTS

Patent Literatures

[PTL 1] Japanese Unexamined Patent Publication No. 2011-2418
[PTL 2] Japanese Unexamined Patent Publication No. 2013-180997
[PTL 3] Japanese Unexamined Patent Publication No. H09-71602
[PTL 4] WO 98/01479
[PTL 5] Japanese Unexamined Patent Publication No. 2005-274350

Non-Patent Literatures

[NPL 1] Journal of Polymer Science Part A: Polymeric Chemistry, 47, pp. 6827-6838, 2009
[NPL 2] Macromolecules, 34, pp. 2248-2256, 2001

SUMMARY OF INVENTION

Technical Problem

The present invention was made in view of the above-described problems in conventional art, and aimed to provide a less stringiness thickener consisting of a compound in high demand as a thickener for cosmetics, i.e., polyacrylic acid or a salt thereof, or PAMPS or a salt thereof, where a stringiness property of the compound was reduced.

Solution to Problem

The present inventors have diligently studied the above-described problems. As a result, the present inventors have found that, in the polyacrylic acid or a salt thereof, or PAMPS or a salt thereof having the weight-average molecular weight of 500 thousand to 8 million, the stringiness property displayed by the compound can be significantly reduced by allowing the content of the compound having the molecular weight of 10 million or higher to be 10 mass % or less. In addition, the present inventors have found that the cosmetics in which the sodium polyacrylate or sodium PAMPS, having a low stringiness property, of the present invention is blended, the stringy feeling, sliminess, and stickiness are hardly felt and the spreadability is excellent, thus leading to the completion of the present invention.

That is, the present invention provides a less stringiness thickener consisting of a polymer having a weight-average molecular weight between 500 thousand and 8 million, wherein said polymer contains not more than 10% by mass of the same having the molecular weight of 10 million or higher, and said polymer is selected from the group consisting of polyacrylic acid, a salt of polyacrylic acid, PAMPS, and a salt of PAMPS.

The present invention also provides a cosmetic raw material including a less stringiness thickener consisting of a polymer having a weight-average molecular weight between 500 thousand and 8 million, wherein said polymer contains not more than 10% by mass of the same having the molecular weight of 10 million or higher, and said polymer is selected from the group consisting of polyacrylic acid, a salt of polyacrylic acid, PAMPS, and a salt of PAMPS.

Furthermore, the present invention provides a cosmetic including a less stringiness thickener consisting of a polymer having a weight-average molecular weight between 500 thousand and 8 million,
wherein said polymer contains not more than 10% by mass of the same having the molecular weight of 10 million or higher, and said polymer is selected from the group consisting of polyacrylic acid, a salt of polyacrylic acid, PAMPS, and a salt of PAMPS.

Advantageous Effects of Invention

According to the present invention, a less stringiness thickener consisting of polyacrylic acid or a salt thereof, or PAMPS or a salt thereof, which has a low stringiness property, generates almost no stringy feeling, sliminess, and stickiness, and is excellent in spreadability, can be obtained. Thus, the cosmetics that are improved in the stringy feeling, sliminess, and stickiness and excellent in spreadability can be prepared by using this less stringiness thickener.

DESCRIPTION OF EMBODIMENTS

Hereinbelow, preferred embodiments of the present invention will be described in detail.
[Synthetic Polymer Compounds]
The polyacrylic acid or a salt thereof and PAMPS or a salt thereof usable in the present invention are those having the weight-average molecular weight of 300 thousand to 8 million, preferably 500 thousand to 8 million, and the content of the compound having the molecular weight of 10 million or higher being 10 mass % or less. This is because if the weight-average molecular weight is less than 300 thousand, the spreadability tends to be poor, and if the weight-average molecular weight exceeds 8 million, it becomes technically difficult to suppress the content of the compound having the molecular weight of 10 million or higher to be 10 mass % or less. As described later, if the content of the compound having the molecular weight of 10 million or higher exceeds 10 mass %, the stringiness property becomes severe, and a stringy feeling, sliminess, and the stickiness are likely generated; thus it is not desirable.

Furthermore, in the synthetic polymer compound of the present invention, if the content of the compound having the molecular weight that is three times or higher of the weight-average molecular weight is 10 mass % or less, the stringiness property tends to be further suppressed; thus it is desirable.

In addition, the molecular weight distribution (namely, weight-average molecular weight/number-average molecular weight) of the synthetic polymer compound of the present invention is preferably 2.0 or lower and more preferably 1.0 to 1.8. This is because if the molecular weight distribution exceeds 2.0, the stringiness property may become prominent.

Examples of the above-described kinds of salts include alkali metal salts (for example, sodium salt, potassium salt, magnesium salt, calcium salt, etc.), organic amine salts (for example, monoethanolamine salt, diethanolamine salt, triethanolamine salt, triisopropanolamine salt, etc.), and the salts of basic nitrogen-containing compounds such as 2-amino-2-methyl-1-propanol, 2-amino-2-methyl-1,3-propanediol, 2-amino-2-hydroxymethyl-1,3-propanediol, L-arginine, L-lysine, and L-alkyl taurine. Among them, monovalent alkali metal salts and organic amine salts are preferable, more preferably a sodium salt, potassium salt and triethanolamine salt, and most preferably a sodium salt.

In the present invention, the polyacrylic acid salt or PAMPS salt indicates the compound obtained by neutralizing the polyacrylic acid or PAMPS with the above-described base (namely, the above-described alkali metals, organic amines, basic nitrogen-containing compounds, etc.) or the compound obtained by polymerizing the acrylic acid or 2-acrylamide-2-methylpropanesulfonic acid (hereinafter abbreviated as AMPS) whose acid section is beforehand neutralized with the above-described base.

In this application, only the polyacrylic acid or a salt thereof and PAMPS or a salt thereof, which are known to have a strong stringiness property, are explained concretely. However, the reduction of the stringiness property is possible, for the synthetic polymer compounds other than these, by allowing the content of the compound having the molecular weight of 10 million or higher to be 10 mass % or less under the conditions that the weight-average molecular weight is 500 thousand to 8 million.

As the examples of such synthetic polymer compounds, those synthesizable by the later-described RAFT polymerization method are preferable. Examples include homopolymers and/or salts thereof in which acrylic acid monomers such as methacrylic acid, alkyl acrylates, alkyl methacrylates, acrylic acid esters; acrylamide monomers such as acrylamide and dimethylacrylamide; vinyl monomers such as vinyl alcohol, vinylpyrrolidone, vinyl acetate, carboxyvinyl, and vinyl methyl ether; and styrene, urethane, etc. are the constituent unit monomer; and copolymers and/or salts thereof consisting of two kinds or more of the monomers selected from these monomers, acrylic acid, and AMPS. Among them, those in which the constituent unit is an acrylic acid monomer or acrylamide monomer are especially preferable. Furthermore, macro-monomers in which polyethylene glycol, silicone-based polymer compound, etc. are added to the above-described monomer, as the side chain, can also suitably be used as the constituent unit.

Specific compound examples include polyacrylamide, polydimethylacrylamide, polyvinyl alcohol, polyvinylpyrrolidone, polyvinylmethyl ether, polyvinyl acetate, carboxyvinyl polymer, etc.; and (acrylic acid/alkyl acrylate) copolymer, (acrylic acid/alkyl methacrylate) copolymer, (alkyl acrylate/styrene) copolymer, polyacrylic acid ester copolymer, (dimethylacrylamide/2-acrylamido-2-methylpropanesulfonic acid) copolymer and salts thereof.
[Synthesis Methods of Polymer Compounds]
The synthetic polymer compound of the present invention can be synthesized by a publicly known living polymerization method. Examples of living polymerization include living anionic polymerization, living cationic polymerization, living radical polymerization (precise radical polymerization, or controlled radical polymerization), etc.

Examples of living radical polymerization include (radical) polymerization that is mediated by nitroxide, or nitroxide-mediated (radical) polymerization (NLRP), atom transfer radical polymerization (ATRP), reversible addition-fragmentation chain transfer (RAFT) polymerization, etc. Examples of atom transfer radical polymerization (ATRP) include electron transfer generated activator ATRP, or activators generated by electron transfer ATRP (AGET ATRP), electron transfer regenerated activator ATRP, or activators regenerated by electron transfer ATRP (ARGET ATRP), initiators to continuously regenerate active species ATRP, or initiators for continuous activator regeneration ATRP (ICAR ATRP), and reverse ATRP (Reverse ATRP). As a derivative technology of the reversible addition-fragmentation chain transfer (RAFT) polymerization, living radical polymerization in which organic tellurium is the growing end, or organic tellurium-mediated living radical polymerization (TERP), antimony-mediated living radical polymerization (SBRP), and bismuth-mediated living radical polymerization (BIRP) can be listed. Examples of other living radical polymerizations include iodine transfer radical polymerization (IRP), cobalt-mediated radical polymerization (CMRP), etc.

The direct polymerization of acrylic acid is preferable because of the simplicity of polymerization. However, when the polymerization is difficult because of the formation of insoluble salts such as catalysts, protected acrylic acid esters such as t-butyl acrylate, methoxymethyl acrylate, and methyl acrylate are used, and the desired polymer compound can be obtained by the succeeding deprotection.

In the present invention, the reversible addition-fragmentation chain transfer polymerization method (RAFT polymerization method) is preferable because the precision synthesis (namely, the synthesis of polymer compounds with narrow molecular weight distribution) is possible (PTL 4). Preferable chain transfer agents are of dithio-type and trithio-type. A polymerization initiator that has a similar chemical structure as that of the chain transfer agent is preferable, and an azo initiator is preferable. The polymerization solvent is not limited in particular, and those having high solubility of monomers and polymers are suitably selected. The polymerization time is preferably several hours to 50 hours.

[Measurement Methods of Molecular Weights]

The molecular weight of the polymer compound synthesized by the method of the present invention can be measured by publicly known methods, such as a light scattering method, an ultracentrifugal method, and a chromatographic method, for the weight-average molecular weight; and an osmometric method and a chromatographic method, for the number-average molecular weight. Among them, the chromatographic method is preferable because the weight-average molecular weight, the number-average molecular weight, and the molecular weight distribution can easily be obtained with a small amount of sample; in particular, a gel permeation chromatographic method (hereinafter abbreviated as GPC) is preferable.

The molecular weight distribution used in this application is the value determined by dividing the weight-average molecular weight obtained by GPC analysis by the number-average molecular weight.

[Usage]

Polyacrylic acid or a salt thereof, and PAMPS or a salt thereof of the present invention can be blended into various cosmetics as a less stringiness thickener or as a cosmetic raw material with low stringiness property. The most preferable blending method is the substitution of the commercial polyacrylic acid or a salt thereof, or PAMPS or a salt thereof whose molecular weight is not suitably controlled. By the substitution, unpleasant usability such as a stringy feeling, sliminess, stickiness, and poor spreadability, of the cosmetics containing the above-described commercial products, can be improved. The synthetic polymer compound of the present invention has a low stringiness property, and the above-described unpleasant usability is not present; therefore, more material can be blended than the corresponding commercial product.

In addition, the polyacrylic acid or a salt thereof and PAMPS or a salt thereof of the present invention can be suitably blended as a substitute for the thickener of other compounds whose molecular weight is not controlled. In particular, it is preferable to blend them into cosmetics as a substitute for the thickener that is known to have a strong stringiness property; specifically, synthetic polymer compounds such as carboxyl polymers, polyethylene glycol, and polyvinyl alcohol; semi-synthetic polymer compounds such as methylcellulose, ethylcellulose, carboxymethylcellulose, and hydroxyethylcellulose; and natural polymer compounds such as carrageenan, xanthan gum, guar gum, and hyaluronic acid or a salt thereof.

The polyacrylic acid or a salt thereof and PAMPS or a salt thereof of the present invention can be blended, as a guide, preferably 0.01 to 5.0 mass % with respect to the total cosmetic, and more preferably 0.05 to 2.5 mass %.

The polyacrylic acid or a salt thereof and PAMPS or a salt thereof of the present invention can be suitably blended in makeup cosmetics such as foundation, eyeshadow, eyeliner, mascara, eyebrow, lip liner, and pre-makeup; and skin care cosmetics such as cream, milky lotion, lotion, gel, pack, and mask.

These products can be produced by the normal method; however, the present invention is not limited by these products.

EXAMPLES

The present invention is described below in more detail with reference to examples, however, the scope of the present invention is not limited thereto. In the following examples, the weight average molecular weight and the number average molecular weight of a polymer compound are sometimes referred to as Mw and Mn, respectively.

Example 1: Precision Synthesis of Sodium Polyacrylate and Sodium PAMPS

By the RAFT polymerization method, which is a living radical polymerization, six kinds of sodium polyacrylate with different weight-average molecular weights and four kinds of sodium PAMPS with different weight-average molecular weights were precision-synthesized. Detailed procedures are shown below. In the below-described synthesis reactions, 4,4'-azobis-(4-cyanovaleric acid) (V-501, manufactured by Wako Pure Chemical Industries, Ltd.) was used as the polymerization initiator, and 4-cyanopentanoic acid dithiobenzoate (synthesized according to NPL 1, hereinafter abbreviated as CPD) was used as the chain transfer agent. As the chain transfer agent, α-(methyltrithiocarbonate)-S-phenylacetic acid (synthesized according to NPL 2, normally abbreviated as MTPA) may also be used.

<Precision-Synthesized Sodium Polyacrylate-1>

Acrylic acid (2511 mg) and V-501 (0.17 mg) were dissolved in ion-exchanged water (9 mL), a methanol solution (1 mL) in which CPD (0.17 mg) had been dissolved was added, and a polymerization reaction was carried out under an argon atmosphere at 60° C. for 24 hours. After the polymerization reaction, sodium hydroxide aqueous solution was added for adjusting the pH to 6.0 to 7.0 (=complete neutralization), and then the mixture was dialyzed against purified water for 4 days. Precision-synthesized sodium polyacrylate-1 (1.82 g, yield: 72%) was collected by freeze-drying. As a result of GPC analysis, the weight-average molecular weight was 7.3 million, and the molecular weight distribution was 1.2.

<Precision-Synthesized Sodium Polyacrylate-2>

Acrylic acid (2504 mg), methylenebisacrylamide (38.4 µg), and V-501 (0.68 mg) were dissolved in ion-exchanged water (9 mL), a methanol solution (1 mL) in which CPD (0.68 mg) had been dissolved was added, and a polymerization reaction was carried out under an argon atmosphere at 60° C. for 24 hours. After the polymerization reaction, sodium hydroxide aqueous solution was added for neutralizing the pH completely, and then the mixture was dialyzed against purified water for 4 days. Precision-synthesized sodium polyacrylate-2 (1.71 g, yield: 68%) was collected by freeze-drying. As a result of GPC analysis, the weight-average molecular weight was 6.33 million, and the molecular weight distribution was 1.4.

<Precision-Synthesized Sodium Polyacrylate-3>

Acrylic acid (2514 mg), methylenebisacrylamide (9.6 µg), and V-501 (0.17 mg) were dissolved in ion-exchanged water (9 mL), a methanol solution (1 mL) in which CPD (0.17 mg) had been dissolved was added, and a polymerization reaction was carried out under an argon atmosphere at 60° C. for 24 hours. After the polymerization reaction, sodium hydroxide aqueous solution was added for neutralizing the pH completely, and then the mixture was dialyzed against purified water for 4 days. Precision-synthesized sodium polyacrylate-3 (1.99 g, yield: 79%) was collected by freeze-drying. As a result of GPC analysis, the weight-average molecular weight was 3.26 million, and the molecular weight distribution was 1.7.

<Precision-Synthesized Sodium Polyacrylate-4>

CPD (0.120 mg) and V-501 (0.120 mg) were dissolved in a methanol solution (120 mL) in which acrylic acid (120 g) had been added. The mixture was degassed with argon for 24 hours, and then a polymerization reaction was carried out at 60° C. for 96 hours. After that, the reaction mixture was subjected to a partial neutralization using sodium hydroxide. Precision-synthesized sodium polyacrylate-4 (75.6 g, yield: 63%) was purified by re-precipitation using water/ethanol, and collected by drying under reduced pressure. As a result of GPC analysis, the weight-average molecular weight was 695 thousand, and the molecular weight distribution was 1.3.

<Precision-Synthesized Sodium Polyacrylate-5>

CPD (21.4 mg) and V-501 (8.7 mg) were dissolved in a methanol solution (69.94 mL) in which acrylic acid (10 g) had been added. The mixture was degassed with argon for 30 min, and then a polymerization reaction was carried out at 60° C. for 44 hours. After confirming the conversion (44.4%) by NMR measurement, sodium hydroxide aqueous solution was added for neutralizing the pH completely. The mixture was dialyzed against purified water for 2 days, and then precision-synthesized sodium polyacrylate-5 (3.65 g, yield: 36.5%) was collected by freeze-drying. As a result of GPC analysis, the weight-average molecular weight was 210 thousand, and the molecular weight distribution was 0.2.

<Precision-Synthesized Sodium Polyacrylate-6>

CPD (193.6 mg) and V-501 (77.6 mg) were dissolved in a methanol solution (69.46 mL) in which acrylic acid (10 g) had been added. The mixture was degassed with argon for 30 min, and then a polymerization reaction was carried out at 60° C. for 44 hours. After confirming the conversion (43.4%) by NMR measurement, sodium hydroxide aqueous solution was added for neutralizing the pH completely. The mixture was dialyzed against purified water for 2 days, and then precision-synthesized sodium polyacrylate-6 (3.82 g, yield: 38.2%) was collected by freeze-drying. As a result of GPC analysis, the weight-average molecular weight was 20 thousand, and the molecular weight distribution was 1.1.

<Precision-Synthesized Sodium PAMPS-1>

AMPS (2500 mg), the pH of which had been adjusted to 7.0 by sodium hydroxide, and V-501 (0.84 mg) were dissolved in ion-exchanged water (9 mL), a methanol solution (1 mL) in which CPD (0.17 mg) had been dissolved was added, and a polymerization reaction was carried out under an argon atmosphere at 60° C. for 24 hours. After the polymerization reaction, the mixture was dialyzed against purified water for 4 days. Precision-synthesized sodium PAMPS-1 was collected by freeze-drying. As a result of GPC analysis, the weight-average molecular weight was 4.03 million, and the molecular weight distribution was 1.4.

<Precision-Synthesized Sodium PAMPS-2>

AMPS (2510 mg), the pH of which had been adjusted to 7.0 by sodium hydroxide, and V-501 (0.70 mg) were dissolved in ion-exchanged water (9 mL), a methanol solution (1 mL) in which CPD (0.70 mg) had been dissolved was added, and a polymerization reaction was carried out under an argon atmosphere at 60° C. for 24 hours. After the polymerization reaction, the mixture was dialyzed against purified water for 4 days. Precision-synthesized sodium PAMPS-2 was collected by freeze-drying. As a result of GPC analysis, the weight-average molecular weight was 2.24 million, and the molecular weight distribution was 1.2.

<Precision-Synthesized Sodium PAMPS-3>

AMPS (9.98 g), the pH of which had been adjusted to 6.0 by sodium hydroxide, and V-501 (0.001 g) were dissolved in ion-exchanged water (40 mL), a methanol solution (3.78 mL) in which CPD (0.027 g) had been dissolved was added, and a polymerization reaction was carried out under an argon atmosphere at 70° C. for 16 hours. After the polymerization reaction, the mixture was dialyzed against purified water for 2 days. Precision-synthesized sodium PAMPS-3 (8.5 g, yield: 85.1%) was collected by freeze-drying. As a result of GPC analysis, the weight-average molecular weight was 13 thousand, and the molecular weight distribution was 1.4.

<Precision-Synthesized Sodium PAMPS-4>

AMPS (9.98 g), the pH of which had been adjusted to 6.0 by sodium hydroxide, and V-501 (0.01 g) were dissolved in ion-exchanged water (40 mL), a methanol solution (3.78 mL) in which CPD (0.27 g) had been dissolved was added, and a polymerization reaction was carried out under an argon atmosphere at 70° C. for 16 hours. After the polymerization reaction, the mixture was dialyzed against purified water for 2 days. Precision-synthesized sodium PAMPS-4 (9.2 g, yield: 92.9%) was collected by freeze-drying. As a result of GPC analysis, the weight-average molecular weight was 1.5 thousand, and the molecular weight distribution was 1.1.

[Measurement of Molecular Weight]

The polyacrylic acid and PAMPS sodium, which were precision-synthesized by the above-described methods, were filtered through a pre-filter (DISMIC-13HP PTFE filter, pore size 0.45 µm, manufactured by Advantec Co., Ltd.). Then, GPC analysis was carried out to measure the molecular weight of those compounds.

<Condition of GPC Measurement>

Guard column: Shodex OHpak SB-G, 1 column (manufactured by Showa Denko Co., Ltd.), Column: Shodex OHpak SB-804HQ, 2 columns (manufactured by Showa Denko Co., Ltd.),
Column temperature: 40° C.,
Column oven: CTO-10ASVP (Shimadzu Corporation),
Degassing equipment: ERC-3215α (manufactured by ERC Co., Ltd.),
Pump: DP-8020 dual pump (manufactured by Tosoh Co., Ltd.),
Refractive index detector: RI-8020 differential refractometer (manufactured by Tosoh Co., Ltd.),
Eluting solvent: 5 mM phosphate buffer (pH 8.0) supplemented with 90% acetonitrile Region 3: compound whose molecular weight is two times or lower of the weight-average molecular weight—equal to the weight-average molecular weight or higher, Region 4: compound whose molecular weight is equal to the weight-average molecular weight or lower—one half of the weight-average molecular weight or higher, Region 5: compound whose molecular weight is one half or lower—one third or higher of the weight-average molecular weight, Region 6: compound whose molecular weight is one third or lower of the weight-average molecular weight.

TABLE 1

| Region | Sample | Retention time (min) | Area (mV × sec) | Height (mV) | Area percentage (%) | Number average molecular weight | Weight average molecular weight | Z-average molecular weight | Molecular weight distribution |
|---|---|---|---|---|---|---|---|---|---|
| 1-6 | Precision-synthesized sodium polyacrylate-2 | 8.710-10.210 | 78.789 | 8.936 | 100.000 | 4870162 | 6330281 (=Mw) | 8236702 | 1.449 |
| 1 | Compound whose molecular weight is three times or higher of the Mw | 8.710-8.908 | 1.558 | 0.503 | 1.977 | 16540755 | 16724830 | 16933431 | 1.011 |
| 2 | Compound whose molecular weight is three times or lower-two times or higher of the Mw | 8.908-9.008 | 5.686 | 1.546 | 7.216 | 12475582 | 12543159 | 12612919 | 1.005 |
| 3 | Compound whose molecular weight is two times or lower of the Mw-equal to the Mw | 9.008-9.125 | 15.149 | 2.290 | 19.227 | 9402217 | 9480431 | 9559978 | 1.008 |
| 4 | Compound whose molecular weight is equal to the Mw or lower-one half of the Mw | 9.125-9.367 | 27.475 | 2.285 | 34.872 | 6137715 | 6300806 | 6462447 | 1.027 |
| 5 | Compound whose molecular weight is one half or lower-one third or higher of the Mw | 9.367-9.625 | 17.627 | 1.516 | 22.373 | 3492423 | 3589407 | 3684301 | 1.028 |
| 6 | Compound whose molecular weight is one third or lower of the Mw | 9.625-10210 | 11.294 | 0.796 | 14.335 | 1780281 | 1892983 | 1990517 | 1.063 |

Flow rate: 0.6 ml/min,
Injection volume: 10 μl,
Molecular weight standard: sodium polystyrene sulfonic acid, standard.

Figure 1:
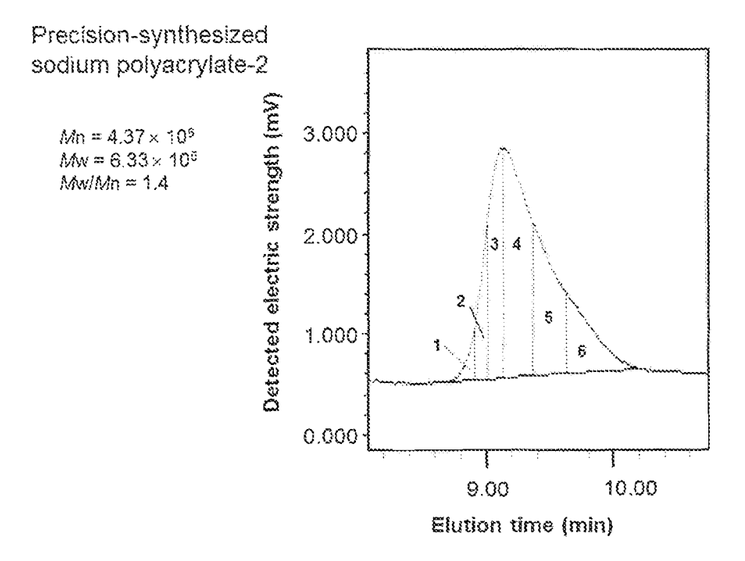
FIG. 1 A chart of gel permeation chromatography (GPC) analysis of the sodium polyacrylate in the present invention (Precision-synthesized sodium polyacrylate-2).

Example 2: Molecular Weight Distribution of Precision-Synthesized Sodium Polyacrylate and Sodium PAMPS The elution peak obtained in the GPC analysis of the above-described precision-synthesized sodium polyacrylate-2 (GPC analysis chart) is shown in FIG. 1. The weight-average molecular weight is $6.33 \times 10^6$, and the number-average molecular weight is $4.37^6 \times 10^6$; therefore, the molecular weight distribution (weight-average molecular weight/number-average molecular weight) is 1.4. Accordingly, the precision-synthesized sodium polyacrylate-2 synthesized by the method of the present invention is seen to be a uniform molecular weight compound.

In the following, the above-described GPC analysis chart was divided into six regions for the respective compounds having the below-described molecular weights (FIG. 1), and the area percentages of the respective regions were determined. The results are shown in Table 1.
Region 1: compound whose molecular weight is three times or higher of the weight-average molecular weight,
Region 2: compound whose molecular weight is three times or lower—two times or higher of the weight-average molecular weight, The area percentage in Table 1 indicates the percentage of the eluted compound, having the concerned molecular weight, with respect to the total amount of the precision-synthesized sodium polyacrylate-2. Accordingly, the percentage of the compound with the molecular weight of three times or higher of the weight-average molecular weight is obtained as the area percentage of Region 1 (=1.977%). The percentage of the compound with the molecular weight of two times or higher of the weight-average molecular weight is obtained as the sum of the area percentages of Region 1 and Region 2 (=1.977+7.216=9.193%). Similarly, the percentage of the compound with the molecular weight of one half or lower of the weight-average molecular weight is obtained as the sum of the area percentages of Region 5 and Region 6 (=22.373+14.335=36.708%). The percentage of the compound with the molecular weight of one third or less of the weight-average molecular weight is obtained as the area percentage of Region 6 (=14.335%).

A similar analysis was carried out for all the above-described precision-synthesized sodium polyacrylate and sodium PAMPS. In addition, the content of giant polymers with the molecular weight of 10 million or higher was also calculated. The results are shown in Table 2 and Table 3.

In addition, a similar analysis was attempted for the commercial sodium polyacrylate and sodium PAMPS that are widely used as the thickener for cosmetics. Generally, the weight-average molecular weight for the commercially available polyacrylic acid or a salt thereof and PAMPS or a salt thereof for cosmetics can be known as the product information; however, the molecular weight distribution is often unknown. Therefore, the filtration was attempted for the above-described commercial product with the above-described prefilter (pore size: 0.45 μm). However, the filtration could not be carried out in all cases because of clogging; thus GPC analysis could not be carried out.

The filtration with a prefilter having a pore size of 0.45 μm is an operation that is normally carried out to remove macromolecules whose analysis is not possible by GPC. In addition, the present inventors have confirmed that 10 mass % solution of a linear water-soluble polymer compound with the weight-average molecular weight of about 10 million can be filtered with such a prefilter. Thus, it is considered that more than 10 mass % of macromolecules with the molecular weight of 10 million or higher are contained in the commercial sodium polyacrylate and sodium PAMPS used in this application.

The polymer compounds used in this analysis are as follows.

Sodium Polyacrylate

Test Example 1

Sodium salt of Carbopol 981 (manufactured by Lubrizol Advanced Materials Co., Ltd.), completely neutralized

Test Example 2

Sodium salt of Synthalen L (manufactured by 3V Sigma), completely neutralized

Test Example 3

Sodium salt of ARONVIS S (manufactured by Japan Pure Chemical), completely neutralized

Test Example 4

Sodium salt of polyacrylic acid (306223, manufactured by Sigma-Aldrich Corporation), completely neutralized

Test Example 5

Sodium salt of polyacrylic acid (306215, manufactured by Sigma-Aldrich Corporation), completely neutralized

Test Example 6

Sodium salt of polyacrylic acid (manufactured by Wako Pure Chemical Industries, Ltd.), completely neutralized

Test Example 7

A mixture of Test Example 1 and Test Example 14 in a ratio of 5:5 by weight

Test Example 8

A mixture of Test Example 1 and Test Example 14 in a ratio of 1:9 by weight

Test Example 11

Precision-synthesized sodium polyacrylate-1

Test Example 12

Precision-synthesized sodium polyacrylate-2

Test Example 13

Precision-synthesized sodium polyacrylate-3

Test Example 14

Precision-synthesized sodium polyacrylate-4

Test Example 15

Precision-synthesized sodium polyacrylate-5

Test Example 16

Precision-synthesized sodium polyacrylate-6

Natural and Semi-Synthetic Polymer Compounds

Test Example 9

KELTROL (manufactured by CP Kelco Co.)

Test Example 10

NATROSOL 250HHR (manufactured by Hercules Inc.)

Sodium PAMPS

Test Example 17

Hostacerin AMPS (manufactured by Clariant)

Test Example 18

Precision-synthesized sodium PAMPS-1

Test Example 19

Precision-synthesized sodium PAMPS-2

Test Example 20

Precision-synthesized sodium PAMPS-3

Test Example 21

Precision-synthesized sodium PAMPS-4

TABLE 2

| Test Example | Sample | Weight average molecular weight (Mw) | Molecular weight distribution (Mw/Mn) | Content of the compound having the following molecular weight | | | | |
|---|---|---|---|---|---|---|---|---|
| | | | | ≥10 million | ≥3 × Mw | ≥2 × Mw | ≥½ × Mw | ≥⅓ × Mw |
| 1 | Commercial sodium polyacrylate-1 | ≥10 million | N.D. | >10.0% | N.D. | N.D. | N.D. | N.D. |
| 2 | Commercial sodium polyacrylate-2 | ≥10 million | N.D. | >10.0% | N.D. | N.D. | N.D. | N.D. |
| 3 | Commercial sodium polyacrylate-3 | 4 million | N.D. | >10.0% | N.D. | N.D. | N.D. | N.D. |
| 4 | Commercial sodium polyacrylate-4 | 3 million | N.D. | >10.0% | N.D. | N.D. | N.D. | N.D. |
| 5 | Commercial sodium polyacrylate-5 | 1.25 million | N.D. | >10.0% | N.D. | N.D. | N.D. | N.D. |
| 6 | Commercial sodium polyacrylate-6 | 1 million | >2 | >10.0% | N.D. | N.D. | N.D. | N.D. |
| 7 | A mixture of Test Example 1 and Test Example 14 in a ratio of 5:5 by weight | unknown | N.D. | >10.0% | N.D. | N.D. | N.D. | N.D. |
| 8 | A mixture of Test Example 1 and Test Example 14 in a ratio of 1:9 by weight | unknown | N.D. | >10.0% | N.D. | N.D. | N.D. | N.D. |
| 9 | Commercial xanthan gum | ≥1 million | N.D. | N.D. | N.D. | N.D. | N.D. | N.D. |
| 10 | Commercial hydroxyethylcellulose | unknown | N.D. | N.D. | N.D. | N.D. | N.D. | N.D. |
| 11 | Precision-synthesized sodium polyacrylate-1 | 7.30 million | 1.2 | 2.7% | ≤2.7% | 2.7% | 12.9% | ≤12.9% |
| 12 | Precision-synthesized sodium polyacrylate-2 | 6.21 million | 1.4 | 9.2% | 2.6% | 9.2% | 36.5% | 14.3% |
| 13 | Precision-synthesized sodium polyacrylate-3 | 3.26 million | 1.7 | 4.7% | 4.7% | 23.7% | 28.2% | 8.8% |
| 14 | Precision-synthesized sodium polyacrylate-4 | 0.70 million | 1.3 | — | 3.7% | 19.9% | 11.8% | 1.9% |
| 15 | Precision-synthesized sodium polyacrylate-5 | 0.21 million | 2.0 | — | 3.7% | 16.1% | 28.8% | 11.2% |
| 16 | Precision-synthesized sodium polyacrylate-6 | 20 thousand | 1.1 | — | ≤5.1% | 5.1% | 3.4% | ≤3.4% |

ND: Not detectable (since the sample did not pass through a prefilter having a pore size of 0.45 mm),
—: below measurable limits As described above, all the commercial sodium polyacrylates are considered to contain 10 mass % or more of macromolecules with the molecular weight of 10 million or higher. Thus, in the commercial sodium polyacrylates in Test Examples 4 to 6, where the weight-average molecular weight is 1 million to 3 million, at least more than 10 mass % of the compound with the molecular weight that is three times or higher of the weight-average molecular weight is considered to be contained. Thus, many of commercial polyacrylic acids and salts thereof, which are widely used as the thickener for cosmetics, are collections of those with non-uniform molecular weights and containing a large amount of compounds having significantly larger molecular weights than the weight-average molecular weight.

On the other hand, the molecular weight distribution of precision-synthesized sodium polyacrylates (Test Examples 11 to 16) prepared in this application was 1.1 to 2.0 and it was narrow in the range of the weight-average molecular weight of 20 thousand to 7.3 million, and the content of macromolecules with molecular weights of 10 million or higher was 9.2 mass % or less. In addition, the content of the compound with the molecular weight of three times or higher or one third or lower of the weight-average molecular weight were 5.1 mass % or less, or 14.3 mass % or less, respectively. From these, the sodium polyacrylate prepared by the method of the present invention is seen to be a collection of those with uniform molecular weights.

TABLE 3

| Test Example | Sample | Weight average molecular weight (Mw) | Molecular weight distribution (Mw/Mn) | Content of the compound having the following molecular weight | | | | |
|---|---|---|---|---|---|---|---|---|
| | | | | ≥1000万 | ≥3 × Mw | ≥2 × Mw | ≥½ × Mw | ≥⅓ × Mw |
| 17 | Commercial sodium PAMPS-1 | ≥10 million | N.D. | >10.0% | N.D. | N.D. | N.D. | N.D. |
| 18 | Precision-synthesized sodium PAMPS-1 | 4.03 million | 1.4 | 3.6% | 3.6% | 22.2% | 16.7% | 5.6% |
| 19 | Precision-synthesized sodium PAMPS-2 | 2.24 million | 1.2 | ≤2.6% | 2.6% | 25.1% | 17.2% | 8.7% |
| 20 | Precision-synthesized sodium PAMPS-3 | 0.13 million | 1.4 | — | 7.6% | 21.4% | 26.7% | 11.2% |
| 21 | Precision-synthesized sodium PAMPS-6 | 15 thousand | 1.1 | — | ≤7.7% | 7.7% | 7.2% | ≤7.2% |

ND: Not detectable (since the sample did not pass through a prefilter having a pore size of 0.45 mm),
—: below measurable limits The molecular weight distribution of the precision-synthesized sodium PAMPS in this application was 1.1 to 1.4 and it was narrow in the range of the weight-average molecular weight of 15 thousand to 4.03 million. The content of macromolecules with the molecular weight of 10 million or higher was 3.6 mass % or less, the content of the compound with the molecular weight that is three times or higher of the weight-average molecular weight was 7.7 mass % or less, and the content of the compound with the molecular weight that is one third or lower of the weight-average molecular weight was 11.2 mass % or less (Table 3). Thus, similarly to the above-described precision-synthesized polyacrylic acid, it was shown to be a collection of those with uniform molecular weights.

Example 3: Evaluation of Stringiness Property and Usability

In the following, the stringiness property and usability are evaluated, for the above-described polymer compounds, according to the methods explained below.
<Evaluation of Stringiness Property>
One mass % solution of each polymer compound was prepared and placed in a container at room temperature. The container was set on a texture analyzer (TA.XT Plus, manufactured by Stable Micro Systems), a round disk with the diameter of about 1 cm was uniformly and lightly contacted on the surface of the above-described solution, and the stringiness behavior of the solution was observed by letting down the container at the velocity of 5 mm/sec. The distance that the container descended, until the cut of the stringiness solution, was measured as the "stringiness length". This stringiness length is the indicator of the stringiness property of polymer compounds, and "the larger the value, the stronger the stringiness property" (PTL 5). In this application, when the stringiness length was 10 mm or less, the stringiness property was judged to be low.
<Evaluation of Usability>
The compositions of the below-described formulations (compositions 1 and 2) were prepared, and the actual application tests were carried out by three expert panelists. They were asked to apply the composition 1 on the right face and the composition 2 on the left face and asked to evaluate the below-described usabilities, according to the criteria below, of the composition 1 by comparing with the composition 2.
Composition 1: A Composition Containing a Polymer Compound

| | |
|---|---|
| Polymer compound | 0.1 mass g |
| Glycerin | 15.0 mass g |
| Purified water | 84.9 mass g |

Composition 2: A Composition Containing No Polymer Compound

| | |
|---|---|
| Glycerin | 15.0 mass g |
| Purified water | 85.0 mass g |

Stringy Feeling
A: Three out of three panelists agreed that neither composition provided any stringy feeling.
B: Two out of three panelists agreed that neither composition provided any stringy feeling.
C: One out of three panelists agreed that neither composition provided any stringy feeling.
D: All three panelists agreed that the composition 1 provided more intense stringiness than the composition 2.
Sliminess
A: Three out of three panelists agreed that neither composition was slimy.
B: Two out of three panelists agreed that neither composition was slimy.
C: One out of three panelists agreed that neither composition was slimy.
D: All three panelists agreed that the composition 1 was much slimier than the composition 2.
Stickiness
A: Three out of three panelists agreed that neither composition was sticky.
B: Two out of three panelists agreed that neither composition was sticky.
C: One out of three panelists agreed that neither composition was sticky.
D: All three panelists agreed that the composition 1 was much stickier than the composition 2.
Spreadability
A: All three panelists agreed that both the composition 1 and the composition 2 provided an excellent spreadability on the skin.
B: Two out of three panelists agreed that both the composition 1 and the composition 2 provided an excellent spreadability on the skin.
C: One out of three panelists agreed that both the composition 1 and the composition 2 provided an excellent spreadability on the skin.
D: All three panelists agreed that the spreadability of composition 1 was inferior to the spreadability of composition 2.

TABLE 4

| Test Example | Sample | Usability | | | | Stringiness property |
|---|---|---|---|---|---|---|
| | | Absence of stringiness feeling | Absence of sliminess | Absence of stickiness | Spreadability | Stringiness length (mm) |
| 1 | Commercial sodium polyacrylate-1 | C | C | C | B | 15 |
| 2 | Commercial sodium polyacrylate-2 | C | C | C | B | 12 |
| 3 | Commercial sodium polyacrylate-3 | D | D | B | A | 20 |
| 4 | Commercial sodium polyacrylate-4 | C | C | B | A | 12 |
| 5 | Commercial sodium polyacrylate-5 | D | C | B | A | 20 |
| 6 | Commercial sodium polyacrylate-6 | D | C | B | A | 20 |
| 7 | A mixture of Test Example 1 and Test Example 14 in a ratio of 5:5 by weight | C | C | C | A | 12 |
| 8 | A mixture of Test Example 1 and Test Example 14 in a ratio of 1:9 by weight | C | C | C | A | 11 |
| 9 | Commercial xanthan gum | C | D | C | A | 13 |
| 10 | Commercial hydroxyethylcellulose | C | D | C | A | 12 |
| 11 | Precision-synthesized sodium polyacrylate-1 | B | B | B | A | 6 |
| 12 | Precision-synthesized sodium polyacrylate-2 | B | B | B | A | 4 |

TABLE 4-continued

| Test Example | Sample | Usability | | | | Stringiness property Stringiness length (mm) |
|---|---|---|---|---|---|---|
| | | Absence of stringiness feeling | Absence of sliminess | Absence of stickiness | Spreadability | |
| 13 | Precision-synthesized sodium polyacrylate-3 | B | B | B | A | 7 |
| 14 | Precision-synthesized sodium polyacrylate-4 | B | B | B | A | 8 |
| 15 | Precision-synthesized sodium polyacrylate-5 | B | A | A | C | 2 |
| 16 | Precision-synthesized sodium polyacrylate-6 | B | A | A | D | 5 |

All of the commercial polymer compounds (commercial sodium polyacrylates (Test Examples 1 to 6), commercial xanthan gum (Test Example 9), and commercial hydroxyethylcellulose (Test Example 10)), which are widely used as the thickener for cosmetics, are high in the stringiness property (stringiness length longer than 10 mm). Even when the composition containing 0.1 mass % thereof (namely, composition 1) is applied on the skin, a stringy feeling and sliminess were present. In addition, the longer the stringiness length of the compound (for example, Test Examples 3, 5, and 6), the stronger the stringy feeling and sliminess; thus it is seen that the stringiness property of the polymer compound and the stringy feeling, which is felt by the human skin, are correlated well.

On the other hand, the stringiness property of all the precision-synthesized sodium polyacrylates of the present invention is low (stringiness length: 10 mm or less). Even when the composition containing 0.1 mass % thereof is applied on the skin, the stringy feeling and sliminess were hardly felt (Test Examples 11 to 16). As described above, the stringiness property of polymer compounds is dependent on viscosity; thus the stringiness property is generally considered to increase with the increase in the weight-average molecular weight. However, in the precision-synthesized sodium polyacrylates (weight-average molecular weight: 7.3 million and 6.21 million, stringiness length: 6 mm and 4 mm) of Test Example 11 and Test Example 12 of this application, the stringiness property and stringy feeling were very low, regardless of the very large weight-average molecular weight, compared with the commercial sodium polyacrylates (weight-average molecular weight: 4 million to 1 million, stringiness length: 12 to 20 mm) of Test Examples 3 to 6.

These results indicate that the stringiness property shown by polymer compounds is also highly controlled by the factors other than the weight-average molecular weight.

Therefore, the change in the stringiness property generated by adding a commercial product to the precision-synthesized product was analyzed. The precision-synthesized sodium polyacrylate-4 (Test Example 14) hardly contains the compound with the weight-average molecular weight of 10 million or higher, and it is a compound with very uniform molecular weights. To this precision-synthesized sodium polyacrylate-4, the commercial polyacrylic acid-1 (Test Example 1) with the weight-average molecular weight of 10 million or higher was added in equal masses. As a result, a high-stringiness compound that displays a stringiness length that is close to the average of those of Test Example 14 and Test Example 1 (stringiness length: 12 mm) was obtained (Test Example 7). This mixture generated a stringy feeling, sliminess, and also stickiness.

Furthermore, a mixture where only 10 mass % of the commercial polyacrylic acid-1 was added to the precision-synthesized sodium polyacrylate-4 was prepared (Test Example 8). Amazingly, the mixture showed a high stringiness property (stringiness length: 11 mm), and the stringy feeling, sliminess, and stickiness were present similarly to the above-described equal-mass mixture (Test Example 7).

These results suggest that if the percentage of the compound with the molecular weight of 10 million or higher exceeds 10 mass %, even in the case of the precision-synthesized polyacrylic acid (or a salt thereof), the stringiness property becomes high, and a stringy feeling, sliminess, and also stickiness are generated.

Accordingly, the stringiness property, stringy feeling, sliminess, and stickiness are considered to be suppressible, for the polyacrylic acid and a salt thereof with the weight-average molecular weight of 8 million or less, by suppressing the content of macromolecules with molecular weights of 10 million or higher to be 10 mass % or less.

In the precision-synthesized polyacrylic acids with the weight-average molecular weight of 210 thousand and 20 thousand (Test Example 15 and Test Example 16), the content of macromolecules was lower than the detection limit; the stringiness property was very low, and a stringy feeling, sliminess, and stickiness were hardly present; however, the spreadability was poor.

Thus, in order to obtain polyacrylic acid or a salt thereof where the stringiness property is low, a stringy feeling, sliminess, and stickiness are not generated, and the spreadability is also excellent when applied on the skin, the content of the compound that has the molecular weight of 10 million or higher within the range of the weight-average molecular weight of 300 thousand to 8 million and preferably within the range of 500 thousand to 8 million, have to be suppressed to 10 mass % or less.

TABLE 5

| Test Example | Sample | Usability | | | |
|---|---|---|---|---|---|
| | | Absence of stringiness feeling | Absence of sliminess | Absence of stickiness | Spreadability |
| 17 | Commercial sodium PAMPS-1 | C | C | C | B |
| 18 | Precision-synthesized sodium PAMPS-1 | B | B | B | A |
| 19 | Precision-synthesized sodium PAMPS-2 | B | B | B | A |

TABLE 5-continued

| Test Example | Sample | Usability | | | |
|---|---|---|---|---|---|
| | | Absence of stringiness feeling | Absence of sliminess | Absence of stickiness | Spreadability |
| 20 | Precision-synthesized sodium PAMPS-3 | B | A | A | C |
| 21 | Precision-synthesized sodium PAMPS-6 | B | A | A | D |

As is clear from Table 3 and Table 5, a stringy feeling, sliminess, and stickiness were hardly generated in all of the precision-synthesized sodium PAMPS that were prepared in this application (Test Examples 18 to 21). However, in the compounds with the weight-average molecular weight of 15 thousand and 130 thousand, the spreadability was poor (Test Example 20 and Test Example 21).

Accordingly, it is also considered that in the PAMPS and a salt thereof with the weight-average molecular weight in the range of 500 thousand to 8 million, the stringiness property is low, a stringy feeling, sliminess, and stickiness are hardly observed, and the spreadability is also excellent if the content of the macromolecule with the molecular weight of 10 million or higher is 10 mass % or less.

It was clarified from the above results that when the content of the compound with the molecular weight of 10 million or higher is suppressed to 10 mass % or less in the polyacrylate or a salt thereof and PAMPS or a salt thereof having the weight-average molecular weight of 500 thousand to 8 million, the stringiness property is low, a stringy feeling, sliminess, and stickiness are hardly generated, and the spreadability is excellent.

The polyacrylic acid or a salt thereof and PAMPS or a salt thereof of the present invention can be suitably used in cosmetics as the cosmetic raw material and preferably as the less-stringiness thickener, where the stringiness property is low and a stringy feeling, sliminess, and stickiness are not present.

In the following, the formulation examples of cosmetics in which the precision-synthesized sodium polyacrylate or sodium PAMPS of the present invention was blended as the thickener are shown. In all the cosmetics, a stringy feeling, sliminess, and stickiness were not felt, and the spreadability was also excellent. In the below-described formulation, POE, POP, and PEG are abbreviations of polyoxyethylene, polyoxypropylene, and polyethylene glycol, respectively. The number in parentheses after POE or POP and the number after the hyphen of PEG represent the respective average addition mole numbers.

Although they are omitted in this application, a stringy feeling and sliminess were present in the cosmetics in which the precision-synthesized sodium polyacrylate or sodium PAMPS, in the below-described formulation examples, was replaced by molecularly non-controlled commercial sodium polyacrylate or sodium PAMPS.

Formulation Example 1: Lotion

| <Formulation> | |
|---|---|
| Component | Blending quantity (% by mass) |
| (1) Precision-synthesized sodium polyacrylate-2 | 0.1 |
| (2) Glycerin | 1.0 |
| (3) Dipropylene glycol | 12.0 |
| (4) Ethanol | 8.0 |
| (5) POE (10) methyl glucoside | 3.0 |
| (6) POE (24) POP (13) decyltetradecyl ether | 0.5 |
| (7) Citric acid | 0.02 |
| (8) Sodium citrate | 0.08 |
| (9) Hydroxypropyl-β-cyclodextrin | 0.5 |
| (10) Thiotaurine | 0.1 |
| (11) Adenosine triphosphate disodium salt | 0.1 |
| (12) Sodium hyaluronate | 0.01 |
| (13) EDTA trisodium salt | 0.01 |
| (14) Paraben | q.s. |
| (15) Fragrance | q.s. |
| (16) Purified water | balance |

<Preparation Method>

Components (6) and (15) were dissolved in component (4), and the resulting mixture is referred to as A. Component (14) was dissolved in component (3), and the resulting mixture is referred to as B. The mixture A and B were dissolved in component (16) in which the remaining components had been dissolved, to obtain a lotion.

Formulation Example 2: Serum

| <Formulation> | |
|---|---|
| Component | Blending quantity (% by mass) |
| (1) Precision-synthesized sodium PAMPS-2 | 0.1 |
| (2) Glycerin | 6.0 |
| (3) Dipropylene glycol | 7.0 |
| (4) 1,3-Butylene glycol | 7.0 |
| (5) Polyethylene glycol (molecular weight: app 1500) | 5.0 |
| (6) POE (10) methyl glucoside | 2.0 |
| (7) Triethylhexanoin | 0.3 |
| (8) PEG-60 hydrogenated castor oil | 0.5 |
| (9) Diisostearate polyglyceryl-2 | 0.4 |
| (10) Tranexamic acid | 1.0 |
| (11) Citric acid | q.s. |
| (12) Phenoxyethanol | q.s. |
| (13) Sodium metaphosphate | q.s. |
| (14) Fragrance | q.s. |
| (15) Purified water | balance |

<Preparation Method>

Components (8), (9), and (14) were dissolved in component (7), and the resulting mixture is referred to as A. Components (12) was dissolved in a mixture of components (3) and (4), and the resulting mixture is referred to as B. Components (2), (5), (6), (10), (11), and (13) were dissolved in component (15), and the resulting mixture was stirred with a homomixer while the mixture A, B, and component (1) were added thereto. The resulting mixture was mixed and emulsified to obtain a serum.

Formulation Example 3: Milk

<Formulation>

| Component | Blending quantity (% by mass) |
|---|---|
| (1) Precision-synthesized sodium polyacrylate-3 | 1.0 |
| (2) Hydrogenated polydecene | 1.0 |
| (3) Dimethyl polysiloxane (6cs) | 1.0 |
| (4) Decamethylcyclopentasiloxane | 2.0 |
| (5) Behenyl alcohol | 0.2 |
| (6) Batyl alcohol | 0.1 |
| (7) Glycerin | 7.0 |
| (8) 1,3-Butylene glycol | 8.0 |
| (9) Ethyl hexane acid cetyl | 2.0 |
| (10) Polysorbate 60 | 0.1 |
| (11) PEG-60 hydrogenated castor oil | 0.1 |
| (12) Citric acid | q.s. |
| (13) Sodium citrate | q.s. |
| (14) Potassium hydroxide | q.s. |
| (15) Sodium metaphosphate | q.s. |
| (16) Ascorbyl glucoside | 2.0 |
| (17) Phenoxyethanol | q.s. |
| (18) Disodium edetate | q.s. |
| (19) Iron oxide | q.s. |
| (20) Purified water | balance |

<Preparation Method>

Components (2)-(6), (9)-(11) were heating dissolved to form A. Component (17) was dissolved in component (8), and the resulting mixture is referred to as B. Components (12)-(15), (18)-(19) were dissolved in component (20), and the resulting mixture was heated and stirred with a homomixer while the mixture A and B were added thereto. To the resulting mixture, component (1) was added and mixed to be emulsified. After that, the resulting mixture was cooled and then component (16) was added thereto to obtain a milk.

Formulation Example 4: Milk

<Formulation>

| Component | Blending quantity (% by mass) |
|---|---|
| (1) Precision-synthesized sodium polyacrylate-3 | 1.0 |
| (2) Hydrogenated polydecene | 1.0 |
| (3) Dimethicone | 1.0 |
| (4) Cyclomethicone | 2.0 |
| (5) Behenyl alcohol | 0.2 |
| (6) Batyl alcohol | 0.1 |
| (7) Glycerin | 7.0 |
| (8) 1,3-Butylene glycol | 8.0 |
| (9) Ethyl hexane acid cetyl | 2.0 |
| (10) Polysorbate 60 | 0.1 |
| (11) PEG-60 hydrogenated castor oil | 0.1 |
| (12) Citric acid | q.s. |
| (13) Sodium citrate | q.s. |
| (14) Potassium hydroxide | q.s. |
| (15) Sodium metaphosphate | q.s. |
| (16) Ascorbyl glucoside | 2.0 |
| (17) Phenoxyethanol | q.s. |
| (18) Disodium edetate | q.s. |
| (19) Iron oxide | q.s. |
| (20) Purified water | balance |

<Preparation Method>

Components (2)-(6), (9)-(11) were heating dissolved to form A. Component (17) was dissolved in component (8), and the resulting mixture is referred to as B. Components (7), (12)-(15), (18)-(19) were dissolved in component (20), and the resulting mixture was heated and stirred with a homomixer while the mixture A and B were added thereto. To the resulting mixture, component (1) was further added and mixed to be emulsified. After that, the resulting mixture was cooled and then component (16) was added thereto to obtain a milk.

What is claimed is:

1. A method of increasing the viscosity of a cosmetic without increasing the stringiness of the cosmetic, comprising thickening said cosmetic by adding an effective viscosity-increasing amount of a polymer selected from the group consisting of polyacrylic acid and salts thereof, wherein:
   (a)
   (b) the polymer is selected from the group consisting of RAFT polymers having a weight average molecular weight between 500 thousand and 8 million;
   (c) not more than 10% by mass of said RAFT polymer consists of molecules having a molecular weight of 10 million or higher;
   (d) the measured stringiness of a 1% w/w aqueous solution of the RAFT polymer is 10 mm or less; and
   (e) the amount of RAFT polymer is between 0.05 and 2.5 mass % relative to the mass of the cosmetic.

2. A method of increasing the viscosity of a cosmetic without increasing the stringiness of the cosmetic, comprising thickening said cosmetic by adding an effective viscosity-increasing amount of a polymer selected from the group consisting of polyacrylic acid and salts thereof, wherein:
   (a) ;
   (b) the polymer is selected from the group consisting of RAFT polymers having a weight average molecular weight between 500 thousand and 8 million;
   (c) not more than 10% by mass of said RAFT polymer consists of molecules having a molecular weight that is more than three times the weight average molecular weight of said RAFT polymer;
   (d) the measured stringiness of a 1% w/w aqueous solution of the RAFT polymer is 10 mm or less; and
   (e) the amount of RAFT polymer is between 0.05 and 2.5 mass % relative to the mass of the cosmetic.

3. The method of claim 1, wherein the weight-average molecular weight of said polymer is between 2.24 million and 8 million.

4. The method of claim 2, wherein the weight-average molecular weight of said polymer is between 2.24 million and 8 million.

5. The method of claim 1, wherein the weight-average molecular weight of said polymer is between 4.03 million and 8 million.

6. The method of claim 2, wherein the weight-average molecular weight of said polymer is between 4.03 million and 8 million.

7. The method of claim 1, wherein the weight-average molecular weight of said polymer is between 6.21 million and 8 million.

8. The method of claim 2, wherein the weight-average molecular weight of said polymer is between 6.21 million and 8 million.

* * * * *